(12) United States Patent
Bene

(10) Patent No.: US 9,095,661 B2
(45) Date of Patent: Aug. 4, 2015

(54) METHOD AND APPARATUS FOR CONTROLLING A FLUID FLOW RATE IN A FLUID TRANSPORT LINE OF A MEDICAL DEVICE

(75) Inventor: Bernard Bene, Irigny (FR)

(73) Assignee: Gambro Lundia AB, Lund (SE)

( * ) Notice: Subject to any disclaimer, the term of this patent is extended or adjusted under 35 U.S.C. 154(b) by 389 days.

(21) Appl. No.: 13/518,588

(22) PCT Filed: Nov. 29, 2010

(86) PCT No.: PCT/IB2010/003051
§ 371 (c)(1),
(2), (4) Date: Aug. 28, 2012

(87) PCT Pub. No.: WO2011/077205
PCT Pub. Date: Jun. 30, 2011

(65) Prior Publication Data
US 2012/0305090 A1    Dec. 6, 2012

(30) Foreign Application Priority Data

Dec. 22, 2009 (EP) .................................. 09015834

(51) Int. Cl.
*F17D 3/00* (2006.01)
*A61M 1/34* (2006.01)
*A61M 1/16* (2006.01)

(52) U.S. Cl.
CPC ............. *A61M 1/342* (2013.01); *A61M 1/1601* (2014.02); *F17D 3/00* (2013.01); *A61M 2205/3396* (2013.01); *A61M 2205/702* (2013.01); *Y10T 137/0324* (2015.04); *Y10T 137/85986* (2015.04)

(58) Field of Classification Search
CPC .......................................................... F17D 3/00
USPC ............. 137/392, 386, 565.3; 417/36, 40, 43, 417/124; 141/198–229
See application file for complete search history.

(56) References Cited

U.S. PATENT DOCUMENTS 3,252,618 A    5/1966   Anderson et al.
3,352,779 A    11/1967  Austin et al.
(Continued)

FOREIGN PATENT DOCUMENTS

DE    38 89 684     9/1994
EP    0 122 604    10/1984
(Continued)

OTHER PUBLICATIONS

Drukker, et al., "Replacement of Renal Function by Dialysis", Fourth edition, 49 pages, copyright 1996.

*Primary Examiner* — John K Fristoe, Jr.
*Assistant Examiner* — Christopher Ballman
(74) *Attorney, Agent, or Firm* — K&L Gates LLP

(57) ABSTRACT

An apparatus for controlling a fluid flow rate in a fluid transport line of a medical device, including at least a first pump, at least a chamber for collecting the fluid, at least a sensor for providing a first value correlated to the amount of fluid in the chamber, and a control device configured for receiving a second value representative of the fluid flow rate through the first pump and for correlating the second value with the first value to obtain an accuracy check of the second value. A method for controlling a fluid flow rate in a fluid transport line of a medical device including pumping a fluid, collecting the fluid in a chamber, sensing a first value correlated to the amount of fluid in the chamber, and detecting and sending a second value representative of the fluid flow rate through the first pump to a control device, sending the first value to the control device, and correlating the second value with the first value to obtain an accuracy check.

27 Claims, 4 Drawing Sheets

(56) References Cited

U.S. PATENT DOCUMENTS

| | | | |
|---|---|---|---|
| 4,372,846 A | 2/1983 | Yamagami et al. | |
| 4,670,007 A | 6/1987 | Wheeldon et al. | |
| 4,747,950 A | 5/1988 | Guinn | |
| 4,850,805 A | 7/1989 | Madsen et al. | |
| 5,306,242 A * | 4/1994 | Joyce et al. | 604/82 |
| 5,316,444 A | 5/1994 | Wicnienski | |
| 5,342,527 A | 8/1994 | Chevallet et al. | |
| 5,402,670 A | 4/1995 | Wicnienski | |
| 5,725,776 A | 3/1998 | Kenley et al. | |
| 6,440,311 B1 | 8/2002 | Rosenqvist et al. | |
| 6,561,996 B1 | 5/2003 | Gorsuch | |
| 6,610,024 B1 | 8/2003 | Benatti | |
| 7,789,850 B2 * | 9/2010 | Roger | 604/29 |
| 7,857,976 B2 * | 12/2010 | Bissler et al. | 210/645 |
| 2003/0132161 A1 * | 7/2003 | Pfeil et al. | 210/646 |
| 2004/0231414 A1 | 11/2004 | Delnevo | |
| 2004/0267183 A1 | 12/2004 | Chevallet | |
| 2009/0173682 A1 | 7/2009 | Robinson et al. | |

FOREIGN PATENT DOCUMENTS

| | | |
|---|---|---|
| EP | 0 128 683 | 12/1984 |
| EP | 0 578 338 | 1/1994 |
| EP | 0 796 997 A1 | 9/1997 |
| EP | 0 796 998 A1 | 9/1997 |
| EP | 1 088 210 | 4/2001 |
| EP | 2 062 605 A1 | 5/2009 |
| GB | 1 404 134 | 8/1975 |
| JP | 2011156 | 1/1990 |
| WO | 88/06466 | 9/1988 |
| WO | 91/15253 A2 | 10/1991 |
| WO | 0009182 A1 | 2/2000 |
| WO | 01/71297 | 9/2001 |
| WO | 02/26291 | 4/2002 |
| WO | 2004/082737 | 9/2004 |
| WO | 2004112869 A1 | 12/2004 |
| WO | 2007/133259 | 11/2007 |

* cited by examiner

METHOD AND APPARATUS FOR CONTROLLING A FLUID FLOW RATE IN A FLUID TRANSPORT LINE OF A MEDICAL DEVICE

RELATED APPLICATION

This application is the U.S. national phase of International Application No. PCT/IB2010/003051 filed 29 Nov. 2010 which designated the U.S. and claims priority to EP 09015834.6 filed 22 Dec. 2009, the entire contents of each of which are hereby incorporated by reference.

TECHNICAL FIELD

The present invention relates to an apparatus and method for controlling a fluid flow rate in a fluid transport line of a medical device. The medical device may be for example a machine for extracorporeal blood treatment or for treatment of renal insufficiency or for receiving and storing liquid from a donor. The liquid may be treatment liquid or may be liquid taken from a patient or donor. The described embodiments are especially useful, but not only, when applied in waste lines or in injection lines of fluid transport lines in medical devices such as dialysis machines or similar.

BACKGROUND

As it is known in the art, patients suffering from kidney failure or renal insufficiency, or patients suffering of particular pathologies should be submitted to specific treatments. More in detail, it is known to treat blood in an extracorporeal circuit in order to carry out ultrafiltration, haemodialysis, haemofiltration, haemodiafiltration, plasmapheresis, blood component separation, blood oxygenation, etc.

Extracorporeal blood treatment means taking the blood from a patient, treating the blood outside the patient, and returning the treated blood to the patient. Normally, blood is removed from a blood vessel, sent into a withdrawal line of an extracorporeal circuit, passed through a blood-treating unit and returned to another or to the same blood vessel.

Extracorporeal blood treatment is typically used to extract undesirable matter or molecules from the patient's blood, and/or to add beneficial matter or molecules, to the blood. Extracorporeal blood treatment is used with patients incapable of effectively eliminating matter from their blood, for example in the case of a patient who is suffering from temporary or permanent kidney failure. These and other patients may undergo extracorporeal blood treatment to add to or to eliminate matter from their blood, to maintain an acid-base balance or to eliminate excess body fluids, for instance. Extracorporeal blood treatment is typically performed by sampling the patient's blood in a continuous flow, by introducing the blood into a primary chamber of a blood-treating unit in which the blood goes through a semi-permeable membrane. The semi-permeable membrane selectively lets the unwanted matter contained in the blood pass through the membrane, from the primary chamber to the secondary chamber, and also selectively lets the beneficial matter contained in the liquid going into the secondary chamber pass through the membrane to the blood going into the primary chamber, according to the type of treatment.

A number of extracorporeal blood treatments may be performed by the same machine. In ultrafiltration (UF) treatment, the unwanted matter is eliminated from the blood by convection through the membrane in the secondary chamber. In haemofiltration (HF) treatment, the blood runs through the semipermeable membrane as in UF, and the beneficial matter is added to the blood, typically by the introduction of a fluid into the blood, either before, or after its passage through the blood-treating unit and before it is returned to the patient. In haemodialysis (HD) treatment, a secondary fluid containing the beneficial matter is introduced into the filter's secondary chamber. The blood's unwanted matter crosses the semi-permeable membrane and penetrates into the secondary fluid, and the beneficial matter of the secondary fluid may cross the membrane and penetrate into the blood.

In haemodiafiltration (HDF) treatment, the blood and the secondary fluid exchange their matter as in HD, and further, matter is added to the blood, typically by introducing a fluid into the treated blood before it is returned to the patient as in HF, and the unwanted matter is also eliminated from the blood by convection.

In each treatment, the secondary fluid goes through the filter's secondary chamber and receives the blood's unwanted matter by means of the membrane. This liquid is then extracted from the filter: it is commonly called waste, and is sent to a drain or to a receptacle then intended to be discharged into a drain.

In fluid transport lines of medical devices, pumps are usually used in order to pump different fluids, such as blood, treatment liquids, waste liquids, along the transport lines. Such pumps may be for example peristaltic pumps, volumetric pumps, piston type pumps, etc. . . . .

Document U.S. Pat. No. 4,747,950 discloses a method and apparatus for controlling ultra filtration during haemodialysis. Such apparatus comprises a receptacle in fluid communication with a reservoir and a first metering pump provided to withdraw fresh dialysate from the reservoir and deliver it to the receptacle, at a predetermined fixed rate. A second pump is provided to withdraw fresh dialysate from the receptacle and to deliver it to a haemodialyzer. A liquid sensing device is included in the receptacle and the second pump is for example a variable flow pump controllable to adjust the rate of flow of the fresh dialysate towards the haemodialyzer in order to maintain the level or volume of fresh dialysate in the receptacle at a predetermined constant level.

Document U.S. Pat. No. 4,372,846 discloses a blood purification system comprising filtrate metering means including a small container with an upper liquid level sensor and a lower liquid level sensor, the container having an inlet channel and an outlet channel provided with a valve. When the container is filled so that the fluid reaches a position above the level where the upper liquid level sensor is located, the valve is opened to discharge the content of the container. When the liquid subsequently reaches a position below the level where the lower liquid level sensor is located, the valve is closed again.

Document U.S. Pat. No. 6,440,311 discloses a system and method for monitoring a dosage pump in a dialysis machine, in which a second pump is arranged between a dosage pump and a source of fluid and a slave chamber is arranged between the dosage pump and the second pump. A level detector is arranged in the slave chamber to detect when the level of fluid in the slave chamber goes below its level due to a stroke of the piston type dosage pump, and a control arrangement is arranged for activating the second pump when the level is below the level detector. The relationship between the flow from the slave chamber to the dosage pump during its suction stroke and the flow to the slave chamber from the second pump is such that the level in the slave chamber never reaches above the level detector.

Document WO 91/15253, having the features according to the preamble of claim 1, relates to a system for weighing and monitoring a flow from multiple fluid sources into a flow system wherein incoming fluid is received in a weighing bag attached to a control system for monitoring the amount of fluid passed through the same weighing bag. According to what described replacement fluid is sent from replacement fluid containers to a weighing bag by opening a respective clamp. A weight scale measures the fluid contained in the weighing bag after the clamp is closed. A replacement fluid pump is then activated and the weight variation in the weighing bag is used to continuously calibrating the replacement fluid pump to compensate for changes in the resiliency of the tubing set caused, for example, by temperature change.

The known devices suffer generally of one or more of the following problems.

It is to be noted that in known extracorporeal blood treatments the determination of the exact fluid flow rate of the various fluids in the transport lines is a critical aspect, since the amount of liquids passing in the lines is strictly correlated to the quality of the medical treatment. In fact, any imprecision in the fluid rate passing in any of the circuit lines can impair the quality of the medical treatment and may also lead to serious consequences for the health of the patient.

Consequently in known medical devices only pumps having a high level of accuracy and reliability shall be used, and in any case it is difficult to check the accuracy of the actual fluid flow rate passing through the pump.

Indeed the control means of the medical machine usually monitors the pumps and/or the flow rates through sensors.

For example the peristaltic pump speed is monitored (with Hall sensors or the like) and is related to the fluid flow rate in the tube that the pumps is acting on.

In any case the control means cannot check the accuracy of said measure and can not determine any mistake in said measure.

Particularly accuracy is affected by several technical features such as correct coupling between tube and pump, other device elements placed along the tube/line, modification of the working parameters, etc. . . . .

SUMMARY

The present embodiments are presented with particular reference to an extracorporeal blood treatment circuit without thereby limiting the scope of the invention to this specific application. The object of the described embodiments is to provide an apparatus and method for controlling a fluid flow rate in a fluid transport line of a medical device having the same functions as currently known devices and further enabling one or more of the described problems to be solved. In particular it is an object to provide an apparatus and method for controlling a fluid flow rate in a fluid transport line of a medical device that allows to check the accuracy of the fluid flow rate measured provided by sensors placed directly on the pump or measured by any fluid flow rate sensor along the line. It is a further auxiliary object to provide an apparatus and method for controlling a fluid flow rate in a fluid transport line of a medical device that is able to determine with high precision the exact fluid flow rate through a fluid transport line, and in case to regulate the flow through a pump or a line according to the results of the check. It is another object to provide an apparatus and method for controlling a fluid flow rate in a fluid transport line of a medical device that may be simply realized and that is not expensive. Other advantages and characteristics of the described method and apparatus will become clear from reading the following description.

The present invention relates to an apparatus and method for controlling a fluid flow rate in a fluid transport line of a medical device, according to the enclosed independent claims or to any of the dependent claims, in any combination between them. The invention further relates to an apparatus according to any of the enclosed apparatus claims, where a control device is operatively connected at least to a first pump and to a sensor. The invention further relates to an apparatus according to any of the enclosed apparatus claims, where a first and/or second pump/s is/are peristaltic pump/s. The invention further relates to an apparatus according to any of the enclosed apparatus claims, where a chamber is defined by a bag apt to contain a fluid. The invention further relates to a fluid infusion line for a medical device, comprising an apparatus for controlling a flow rate according to any of attached apparatus claims, in which the first pump is disposed between the first chamber and a fluid transport line of a medical device and a fluid source is operatively connected to the first chamber on a side opposite to the first pump. The invention further relates to a fluid waste line for a medical device, comprising an apparatus for controlling a flow rate according to any of attached apparatus claims, in which the first pump is disposed between the first chamber and a fluid line or container for fluid to be discharged from a medical device and a fluid waste zone is operatively connected to the first chamber on a side opposite to the first pump. The invention further relates to a blood treatment device comprising an apparatus according to any of the enclosed apparatus claims. The invention further relates to a medical machine, in particular for blood treatment, comprising an apparatus according to any of the enclosed apparatus claims. The invention further relates to a method according to any of attached method claims, in which the first pump is stopped when the second pump is activated. The invention further relates to a method according to any of attached method claims, further comprising the step of stopping the first pump when the second pump is activated, or when the fluid passes through the fluid regulator, at least for one cycle of a plurality of operating cycles. The invention further relates to a method according to any of attached method claims, comprising the step of sensing a first value of weight corresponding to the quantity of fluid in said chamber or the step of sensing a first value of fluid level corresponding to the level of fluid in said chamber. The invention further relates to a method according to any of attached method claims, comprising the step of comparing the duration of at least two corresponding steps or phases in a cyclical repetition of the first pump's or second pump's working steps, in order to verify if the first pump or the second pump are continuing to work correctly. It is to be noted that in the various phases of the cycles above described, at least the duration of the each phase in which a certain pump is working alone should remain the same in the various cycles, and therefore also a check on the duration of such corresponding phases may be carried out to verify that the pump is working correctly and to guarantee the safety of the treatment. The invention further relates to a method for controlling a fluid flow rate in a fluid infusion line of a medical device, comprising the steps of any of attached method claims, in which a step of collecting a fluid passing in a transport line in a first chamber is carried out by collecting the fluid exiting from a first pump. The invention further relates to a method for controlling a fluid flow rate in a fluid waste line of a medical device, comprising the steps of any of attached method claims, in which a step of pumping a fluid through a fluid transport line by a first pump is carried out by pumping away the fluid from a first chamber.

The presently described method and apparatus afford one or more of the following advantages:

- an apparatus and method for controlling a fluid flow rate in a fluid transport line of a medical device according to the invention allow to check the accuracy of the fluid flow rate measured provided directly by the pump or measured by any fluid flow rate sensor along the line;
- an apparatus and method according to the invention are able to determine with high precision the exact fluid flow rate through a fluid transport line;
- an apparatus and method according to the invention allow to regulate the pumps in order to obtain exactly the desired fluid flow rate through a fluid transport line;
- an apparatus and method according to the invention allow to avoid any mistake in the fluid flow rate in a fluid transport line;
- an apparatus and method according to the invention allow to carry out medical treatments with high reliability and to reduce risks for the patient;
- an apparatus and method according to the invention may be simply realized and are not expensive.

BRIEF DESCRIPTION OF THE DRAWINGS

Additional characteristics and advantages of the present method and apparatus will appear with the detailed description of possible, but not exclusive, embodiments of an extracorporeal blood treatment device. This description will be given below with reference to the annexed drawings, which are supplied for information purposes and are thus not limiting.

DETAILED DESCRIPTION

Figure 1:
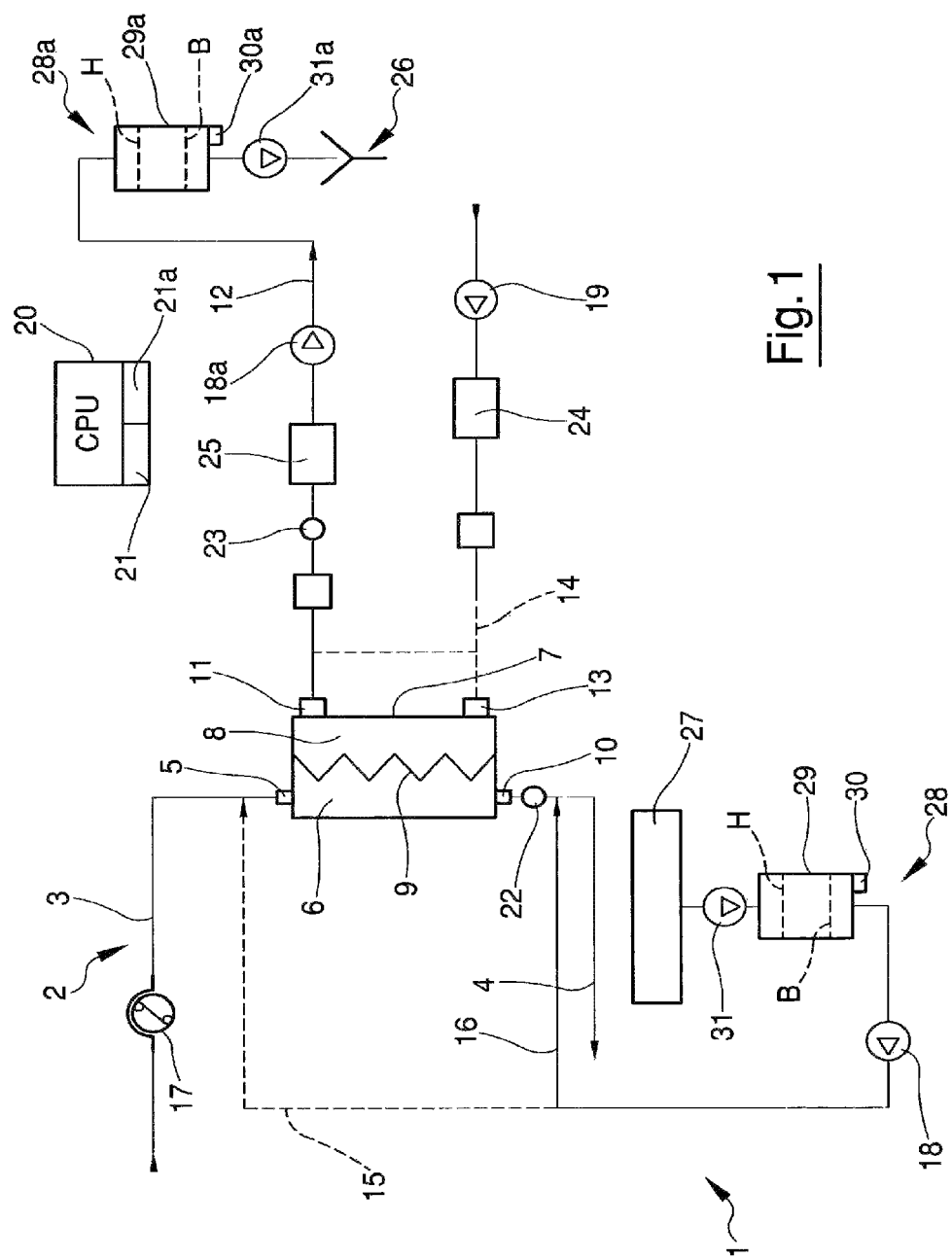
FIG. 1 represents an extracorporeal blood treatment device provided with two apparatuses for controlling a fluid flow rate according to a first and a second embodiment.

With reference to the enclosed drawings a blood treatment equipment has been identified with reference numeral 1.

The equipment or medical device 1 comprises an extracorporeal blood circuit 2 to be connected in use to the cardiovascular system of a patient to be treated (not shown in the drawings). In practice, the patient may be connected to the extracorporeal circuit via one or two needles, a catheter, a cannula, an implanted artificial access device or other equivalent access means, which allows withdrawal and return of blood from and to the patient. The extracorporeal circuit of the embodiment shown in the appended drawings presents a withdrawal line 3, for withdrawing blood to be treated from the patient and a return line 4 for returning treated blood into the patient. A downstream end of the withdrawal line 3 is connected to the inlet 5 of a primary chamber 6 of a treatment unit 7 also comprising a secondary chamber 8 separated from the primary chamber 6 by means of a semipermeable membrane 9. An outlet 10 of the primary chamber 6 of said treatment unit 7 is also connected to an upstream end of the return line 4. The secondary chamber 8 of the treatment unit presents an outlet 11, which is connected to a waste line 12 that leads to a waste end or waste zone 26. In case the equipment is intended to run a hemo-dialysis or hemo-diafiltration treatment the secondary chamber also presents an inlet 13 for receiving a fresh dialysis liquid line 14.

In the embodiment of FIG. 1 the equipment 1 presents a post-infusion line 16 connected to the blood circuit downstream the blood treatment unit 7. Alternatively, or in addition, the equipment may present a pre-infusion line 15 connected to the blood circuit upstream the blood treatment unit. In the blood treatment field the pre-infusion and post-infusion lines are also referred to as pre-dilution and post-dilution lines respectively. The infusion lines take the infusion liquid from a fluid source 27. The fluid source 27 may be a bag containing a proper infusion solution or an on-line prepared fluid coming, for example, from the fresh dialysis inlet line after "proper" filtration. In the embodiment shown the various fluids are in use circulated through the respective lines by the following devices: a blood pump 17 operating on the extracorporeal blood circuit, an infusion pump 18 for the pre-infusion and/or post-infusion lines 15, 16 and a waste pump 18a operating on the waste line 12. If the dialysis line 14 is present and used, the equipment 1 comprises also a fresh liquid pump 19 (in this embodiment the liquid is prepared online, though it is clear for those skilled in the art that infusion or dialysis liquid may come from respective containers of pre-prepared liquid) sending liquid to the dialysis line 14. The pumps 17, 18, 18a, 19 operate according to the instructions received by a control unit 20 of the equipment.

The equipment may comprise further known elements, such as return pressure sensor 22, dialysate pressure sensor 23, flow meters 24 and 25, etc. . . . . The conventional structure and functioning of equipment 1 is not described in further detail in the present description since it is well known to the man skilled in the art.

Also connections between the control unit 20 and the various elements of the circuit (pumps, sensors, actuators, . . . ) are not shown for sake of simplicity.

According to the disclosed embodiments, an apparatus 28, 28a for controlling a fluid flow rate in a fluid transport line of a medical device or equipment 1 is mounted, as an example, on infusion line 16 (or alternatively on infusion line 15) and/or on waste line 12.

Figure 2:
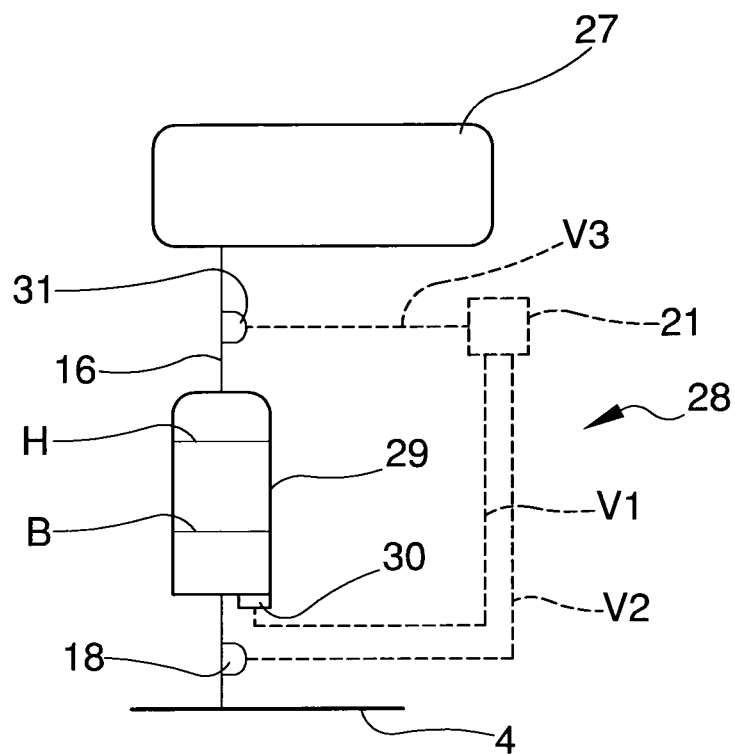
FIG. 2 represents an apparatus according to the first embodiment.
Figure 3:
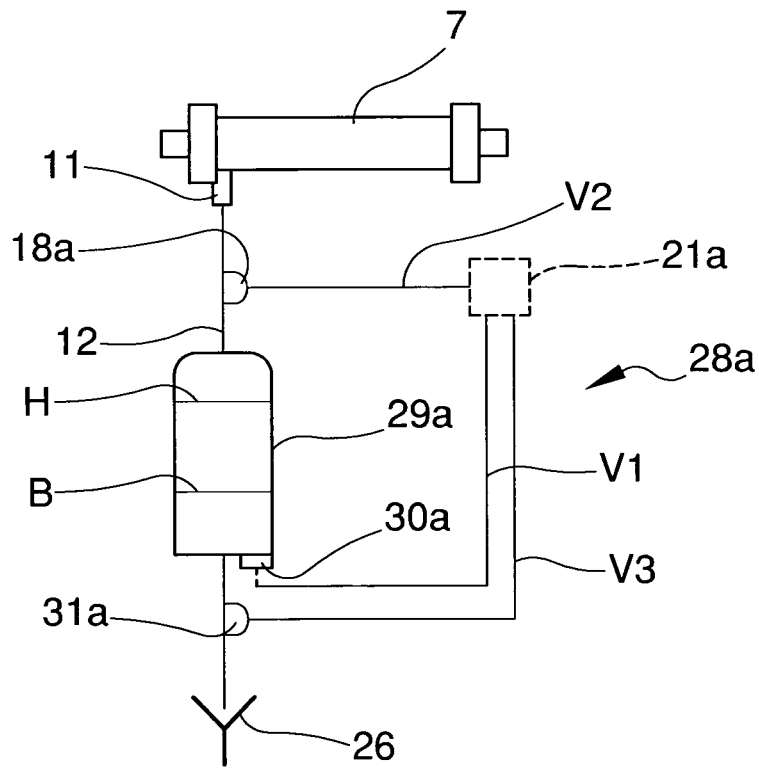
FIG. 3 represents an apparatus according to the second embodiment.

Referring to FIGS. 1, 2 and 3 the apparatus 28, 28a comprises the fluid transport line 12, 15 or 16, at least the first pump 18, 18a disposed in the fluid transport line 12, 15 or 16 for pumping a fluid and at least a first chamber 29, 29a disposed in the fluid transport line 12, 15 or 16 for collecting the fluid. The apparatus 28, 28a further comprises at least a sensor 30, 30a for providing a first value v1 correlated to the amount of fluid in the first chamber 29, 29a. The sensor 30, 30a may be for example a weight sensor configured for controlling the weight of the fluid in the chamber 29, 29a or a level sensor configured for controlling the level of the fluid in the chamber 29, 29a. The sensor 30, 30a may be any other kind of suitable sensor (e.g. a conductivity sensor, etc) adapted to allow determination of the amount of fluid in the chamber 29, 29a. According to a possible embodiment, the first chamber 29, 29a may be defined by a bag apt to contain a fluid, but any kind of receptacle or container may be suitable as well. The apparatus 28, 28a further comprises a control device 21, 21a (for example connected to or integrated into the control unit 20 of the equipment 1) configured for receiving a second value v2 representative of the fluid flow rate through the first pump 18, 18a and for putting into a relation the second value v2 with the first value v1 in order to perform an accuracy check of the second value correctness. In more detail, the control device 21, 21a (which might be defined by the control unit 20 of the equipment) converts the first and/or the second value into homogeneous values (values having the same unit of measurement) which may therefore be compared and consequently may give an index of accuracy of the second value v2.

Advantageously the control device 21, 21a is configured for converting the first value v1 into a fluid flow rate measure and to compare it to the second value v2 in order to obtain the accuracy check of the second value.

Of course if the second value is not a fluid flow rate, the same second value v2 may be converted into a fluid flow rate.

In a possible embodiment, the control device 21, 21a includes technical information regarding the first chamber 29, 29a, so that when receiving from sensor 30, 30a the first value v1 related to the amount of fluid in the first chamber 29, 29a, it is able to convert this level or weight value into a corresponding fluid flow rate value, that is subsequently compared to the second value provided by the first pump 18, 18a (or by another flow sensor). As an example the second value v2 might not be a flow rate, but the fluid flow rate might be obtained (in a standard and known way) from v2 knowing the circuit characteristics (tube section; kind of used pump and its speed).

The control device knows the required circuit parameters and, for example, through a Hall sensor, calculates the actual pump speed (in this case the signal v2 might be the signal coming from the Hall sensor).

With the above data, the control device may calculate the fluid flow rate.

Of course, since some of the inputted and fixed parameters of the circuit might not be accurate or might change during the equipment working, the calculated flow rate (deriving from the second value v2) might be not accurate and consequently an accuracy check is required.

As a possible alternative the second value v2 might be directly a fluid flow rate, measured by a flowmeter for example.

Also in this case, since there could be a sensor drift (or in case of an erroneous calibration), again the second value v2 might not be accurate.

Through the above-mentioned comparison it is possible to obtain a very reliable check of accuracy of the actual flow rate passing through the first pump. According to the disclosed embodiments, it is also possible to regulate the first pump 18, 18a according to the result of this check. In an embodiment, the control device 21, 21a is operatively connected at least to the first pump 18, 18a and to the sensor 30, 30a. Apparatus 28, 28a further comprises a fluid flow regulator 31, 31a disposed in the fluid transport line 12, 15, 16 for regulating the flow rate of the fluid on a side opposite to the first pump 18, 18a with respect to the first chamber 29, 29a, the fluid flow regulator 31, 31a being also operatively connected to the control device 21, 21a. The fluid flow regulator may be for example a valve, a pump, or other suitable element. In the embodiments shown in the attached figures, the fluid flow regulator 31, 31a is a second pump 31, 31a disposed in the fluid transport line 12, 15, 16 for pumping a fluid on a side opposite to the first pump 18, 18a with respect to the first chamber 28, 28a. The second pump 31, 31a is operatively connected to the control device 21, 21a at least to provide a third value v3 representative of the fluid flow rate through the second pump 31, 31a and the control device 21, 21a is also configured for correlating the third value v3 with the first and/or second value in order to obtain an accuracy check of the second and/or third value. In other words, the control device 21, 21a is apt to compare the converted first value v1 as above described with the second or third value v2, v3 (or with converted second or third value), or even the second and the third value (converted or not so as to be homogeneous) with each other in order to check accuracy of such values.

As in the case of the second value v2, also the third value v3 may be the signal coming from the Hall sensor mounted proximate to the corresponding peristaltic pump, or a signal from a flowmeter, for example.

In the first embodiment shown in FIG. 2, the apparatus 28 is applied to an infusion line 15 or 16, in which the first pump 18 is disposed between the first chamber 29 and a fluid transport line 4 of the medical device or equipment 1. In this first embodiment the fluid source 27 is operatively connected to the chamber 29 on a side opposite to the first pump 18.

In the second embodiment shown in FIG. 3, the apparatus 28a is applied to a fluid waste line 12 of the medical device or equipment 1, in which the first pump 18a is disposed between the first chamber 29a and a fluid line or container 7 for fluid to be discharged from a medical device 1. The fluid waste zone 26 is operatively connected to the chamber 29a on a side opposite to the first pump 18a. The first 18, 18a and/or the second pump 31, 31a is/are in detail peristaltic pump/s.

The present description also concerns a method for controlling a fluid flow rate in a fluid transport line of a medical device 1, comprising the steps of pumping a fluid through the fluid transport line 12, 15, 16 by the first pump 18, 18a, collecting the fluid passing in the transport line in the first chamber 29, 29a, sensing the first value correlated to the amount of fluid in the first chamber 29, 29a, detecting and sending the second value representative of the fluid flow rate through the first pump 18, 18a to the control device 21, 21a, sending the first value to the control device 21, 21a, and correlating the second value with the first value in order to obtain an accuracy check of the second value. The method may further comprise the steps of converting the first and/or the second value into homogeneous values; for example to convert the first value v1 into a fluid flow rate measure and comparing it to the second value (if it is a flow rate) in order to obtain the accuracy check of the second value and/or to regulate the first pump 18, 18a accordingly. The method may further comprise the step of regulating a fluid flow rate of the fluid on a side opposite to the first pump 18, 18a with respect to the first chamber 29, 29a. The method may further comprise the steps of pumping the fluid with the second pump 31, 31a disposed in the fluid transport line 12, 15, 16 on a side opposite to the first pump 18, 18a with respect to the first chamber 28, 28a, providing a third value v3 representative of the fluid flow rate through the second pump 31, 31a to a control device 21, 21a, and correlating the third value with the first and/or second values in order to obtain an accuracy check of the second and/or third value. Also the second pump 31, 31a may be regulated according to the result of this check. A method according to what described may further comprise the steps of continuously pumping the fluid by the first pump 18 away from the first chamber 29 during a predetermined treatment period at a predetermined first fluid flow rate, pumping the fluid by the second pump 31, or letting the fluid pass through the fluid regulator 31, at a predetermined second fluid flow rate superior to the predetermined first fluid flow rate, when a predetermined minimum threshold B of the first value is reached, and stopping the second pump 31, or stopping the fluid flow through the fluid flow regulator 31, when a predetermined maximum threshold H of the first value is reached. A method may further comprise the steps of continuously pumping the fluid by the first pump 18a into the first chamber 29a during a predetermined treatment period at a predetermined first fluid flow rate, pumping the fluid by the second pump 31a, or letting the fluid pass through the fluid regulator 31a, at a predetermined second fluid flow rate superior to the predetermined first fluid flow rate, when a predetermined maximum threshold H of the first value is reached, and stopping the second pump 31a, or stopping the fluid flow through the fluid flow regulator 31a, when a predetermined minimum threshold B of the first value is reached.

Figure 4:
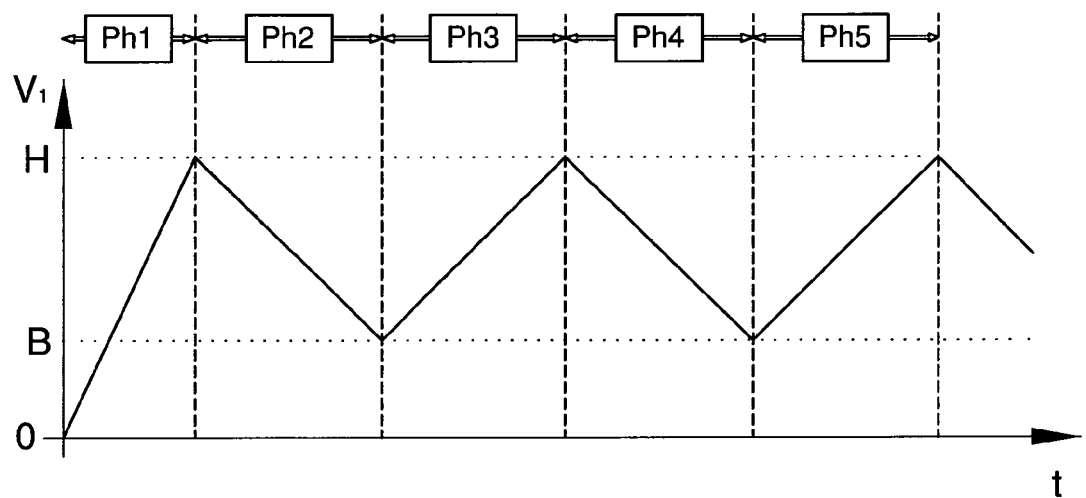
FIG. 4 is a diagram representing the variation of a value representative of the amount of fluid in a first chamber during a first sequence of cycles in the fluid infusion line of FIG. 2.

In other words, according to the methods above described, a first pump 18, 18a is continuously activated during a predetermined treatment period and a predetermined minimum threshold B and a maximum threshold H are provided for the first value, and the fluid flow regulator 31, 31a or second pump 31, 31a are activated by the control device 21, 21a when the minimum threshold B or the maximum threshold H is reached and are vice-versa respectively inactivated when the maximum threshold H or the minimum threshold B are reached, the fluid flow regulator 31, 31a or second pump 31, 31a providing, when activated, a fluid flow rate superior to the fluid flow rate of the first pump 18, 18a. A method according may further comprise the step of repeating cyclically the steps of continuously pumping the fluid by the first pump 18, 18a, pumping the fluid by the second pump 31, 31a, or letting the fluid pass through the fluid regulator 31, 31a, and stopping the second pump 31, 31a, or stopping the fluid flow through the fluid flow regulator 31, 31a. A method according may further comprise the step of stopping the first pump 18, 18a when the second pump 31, 31a is activated, or when the fluid passes through the fluid regulator 31, 31a, at least for one cycle of a plurality of operating cycles. The method may comprise the step of sensing a first value v1 of weight corresponding to the quantity of fluid in the chamber or the step of sensing a first value v1 of fluid level corresponding to the level of fluid in the chamber. When the method is applied to an infusion line, the step of collecting the fluid passing in the transport line 15, 16 in a first chamber 29 is carried out by collecting the fluid exiting from the a first pump 18. When the method is applied to a fluid waste line, the step of pumping the fluid through a fluid transport line 12 by a first pump 18a is carried out by pumping away the fluid from the first chamber 29a. In a first variant the first pump 18, 18a may be stopped when the second pump 31, 31a is activated, while in a second variant the first pump 18, 18a continues working when the second pump 31, 31a is activated and, in this case, the second pump 31, 31a is activated at a flow rate superior to the predetermined first pump's fluid flow rate. Some embodiments of the methods described above are illustrated in detail in FIGS. 4-6. In particular FIG. 4 represents a process carried out on infusion apparatus 28 of FIG. 2 applied to an infusion line 15, 16. The diagram of FIG. 4 represents the variation of the first value v1 representative of the amount of fluid in the first chamber 29 during a first sequence of cycles in the fluid infusion line 15 or 16. The first value v1 is represented in the y-axis and time t is represented in the x-axis. The maximum threshold H may correspond for example to 420 g and the minimum threshold B may correspond to 120 g. In the first phase (or step), indicated as Ph.1 in the figure, only the second pump 31 is activated and working at a constant rate in order to fill the first chamber 29, that is initially completely empty, to the maximum threshold H (passing through the minimum threshold B). When the maximum threshold H is reached by the first value v1, the second pump 31 is stopped and the first pump 18 is activated (beginning of second phase Ph.2) to take away the fluid from the first chamber 29. The first pump 18 is usually activated at a constant rate; and in this case it is activated at a rate (for example 140 ml/min) that is about half of the second pump's rate (for example 280 ml/min). In the third phase Ph.3, starting when the minimum threshold B is reached, the first and the second pump are both activated (and consequently the result is a rate of 140 ml/min filling the first chamber). When the maximum threshold H is reached again the fourth phase Ph.4, identical to the second phase Ph.2, begins, followed by fifth phase Ph.5, identical to third phase Ph.3, and such phases are then repeated cyclically. It is to be noted that the first phase Ph.1 with the second pump 31 working alone allows to compare the first value v1 deriving from the sensor 30 with the third value of flow rate of the second pump 31 and therefore to check the reliability of this value and/or to regulate the second pump 31 accordingly. Analogously, during the second phase Ph.2, the first pump 18 is working alone in order to compare the first value v1 with the second value and therefore to check the reliability of this value and to regulate the first pump 18.

Figure 5:
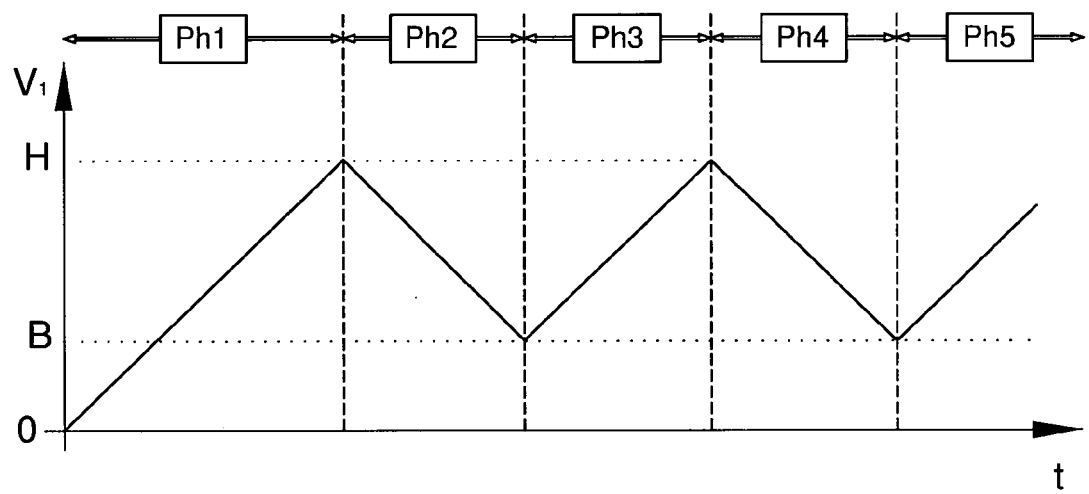
FIG. 5 is a diagram representing the variation of a value representative of the amount of fluid in a first chamber during a second sequence of cycles in the fluid waste line of FIG. 3.
Figure 6:
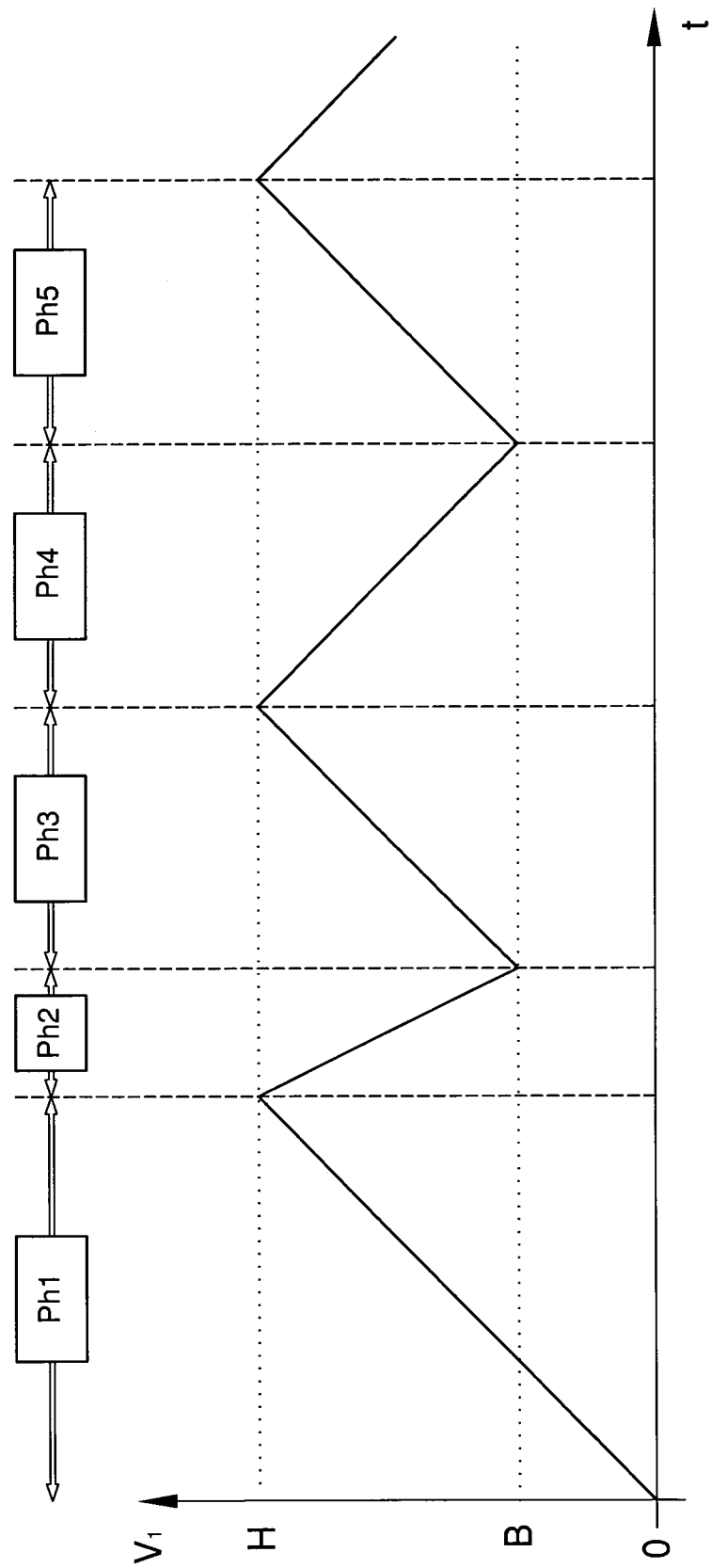
FIG. 6 is a diagram representing the variation of a value representative of the amount of fluid in a first chamber during a third sequence of cycles in the fluid waste line of FIG. 3.

FIG. 5 represents a process carried out on infusion apparatus 28a of FIG. 3 applied to a waste line 12. The diagram of FIG. 5 represents the variation of the first value v1 representative of the amount of fluid in the first chamber 29a during a first sequence of cycles in the waste line 12. The first value v1 is represented in the y-axis and time t is represented in the x-axis. The maximum threshold H may correspond for example to 420 g and the minimum threshold B may correspond to 120 g. In the first phase, indicated as Ph.1 in the figure, only the first pump 18a is activated and working at a constant rate in order to fill the first chamber 29a, that is initially completely empty, to the maximum threshold H (passing through the minimum threshold B). When the maximum threshold H is reached by the first value, the first pump 18a continues working and the second pump 31a is activated (second phase Ph.2) to take away the fluid from the first chamber 29a. The first pump 18a is activated at a constant rate, and also in this case it is activated at a rate (for example 140 ml/min) that is about half of the second pump's rate (for example 280 ml/min). Consequently when both pumps are working, the result is a rate of 140 ml/min taking away the fluid from the first chamber 29a. In the third phase Ph.3, starting when the minimum threshold B is reached, the second pump 31a is stopped and only the first pump 18a is working (as in the first phase). When the maximum threshold H is reached again the fourth phase Ph.4, identical to the second phase Ph.2, begins and is then followed by fifth phase Ph.5, identical to third phase Ph.3, and this sequence of phases is repeated cyclically. It is to be noted that the first phase Ph.1 with the first pump 18a working alone allows to compare the first value v1 deriving from the sensor 30a with the second value of flow rate of the first pump 18a and therefore to check the reliability of this value and/or to regulate the first pump 18a accordingly. During the second phase Ph.2 the second pump 31a is also working, and this allows to compare the first value (correlated in this case to the flow rates of both pumps) with the second value (that has already been checked in the first phase) and third value, and allows therefore also to check the reliability of the values and to regulate also the second pump 31a. FIG. 6 shows a variant of the process of FIG. 5 carried out on apparatus 28a of FIG. 3 applied to a waste line 12. In this variant all phases except the second one are all identical to the corresponding phases of the method of FIG. 5. Only the second phase Ph.2 is different, since in this variant the first pump 18a is stopped when the maximum threshold H is reached and the second pump 31a is activated alone during the second phase until the minimum threshold B is reached. In this was during the second phase Ph.2 the first value (converted into a flow rate value) may be compared directly with the third value and so it is possible to check the reliability of the third value and to regulate the second pump 31a. It is to be noted that in the various phases of the cycles above described, at least the duration of the each phase in which a certain pump is working alone should remain the same in the various cycles, and therefore also a check on the duration of such corresponding phases may be carried out to verify that the pump is working correctly and to guarantee the safety of the treatment.

REFERENCE NUMBERS LIST equipment 1
extracorporeal blood circuit 2
withdrawal line 3
return line 4
primary chamber inlet 5
primary chamber 6
treatment unit 7
secondary chamber 8
semipermeable membrane 9
primary chamber outlet 10
secondary chamber outlet 11
waste line 12
secondary chamber inlet 13
dialysis liquid line 14
pre-infusion line 15
post-infusion line 16
blood pump 17
waste pump (first pump) 18
infusion pump (first pump) 18a
fresh liquid pump 19
control unit 20
control device 21, 21a
return pressure sensor 22
dialysate pressure sensor 23
flow meters 24 and 25
fluid waste end or zone 26
fluid source 27
apparatus 28
chamber 29, 29a
sensor 30, 30a
fluid flow regulator or second pump 31, 31a
first value v1
second value v2
third value v3
maximum threshold H
minimum threshold B

The invention claimed is:

1. An apparatus for controlling a fluid flow rate in a fluid transport line of a medical device comprising:
   a fluid transport line;
   a first pump disposed in said fluid transport line for pumping a fluid;
   a chamber disposed in said fluid transport line for collecting said fluid;
   a sensor for providing a first value correlated to the amount of fluid in said chamber;
   a control device configured for (i) receiving a second value representative of the fluid flow rate through the first pump (ii) converting the first value into a fluid flow rate value, and (iii) determining if the second value is accurate by comparing the fluid flow rate value to the second value; and
   a second pump disposed in said fluid transport line for pumping the fluid and on a side of the fluid transport line opposite to said first pump with respect to said chamber.

2. The apparatus according to claim 1 wherein the second pump disposed in said fluid transport line for pumping fluid on a side opposite to said first pump with respect to said chamber is operatively connected to said control device.

3. The apparatus according to claim 2 wherein said second pump is operatively connected to said control device at least to provide a third value representative of the fluid flow rate through the second pump.

4. The apparatus according to claim 3 wherein said control device is configured for determining if (i) the second value is accurate or (ii) the third value is accurate by putting into relation said third value with said first value.

5. The apparatus according to claim 4 wherein said control device is further configured for regulating said first pump if the determination is that (i) said second value is inaccurate or (ii) the third value is inaccurate.

6. The apparatus according to claim 4 wherein said control device is further configured for regulating said second pump if the determination is that (i) said second value is inaccurate or (ii) the third value is inaccurate.

7. The apparatus according to claim 3 wherein said control device is configured for determining if (i) the second value is accurate or (ii) the third value is accurate by putting into relation said third value with said second value.

8. The apparatus according to claim 2 wherein said first pump is continuously activated during a predetermined treatment period and wherein a predetermined minimum threshold and a maximum threshold are provided for said first value, said second pump being activated by said control device when said minimum threshold or said maximum threshold is reached and being vice versa respectively inactivated when said maximum threshold or said minimum threshold are reached, said second pump providing, when activated, a fluid flow rate superior to the fluid flow rate of said first pump.

9. The apparatus according to claim 1, where the sensor is a weight sensor configured for controlling the weight of the fluid in said chamber or a level sensor configured for controlling the level of the fluid in said chamber.

10. An apparatus according to claim 1 wherein the sensor is a level sensor configured for controlling the level of the fluid in said chamber.

11. A method for controlling a fluid flow rate in a fluid transport line of a medical device comprising:
   pumping a fluid through a fluid transport line by a first pump;
   collecting said fluid passing in said transport line in a chamber;
   sensing the amount of fluid in said chamber and generating a first value representative of the amount of the fluid in said chamber which is sent to a control device;
   detecting and sending a second value representative of a fluid flow rate through the fluid transport line to a control device;
   converting the first value into a fluid flow rate value;
   determining if the second value is accurate by comparing the fluid flow rate value to the second value; and
   pumping the fluid with a second pump disposed in said fluid transport line on a side opposite to said first pump with respect to said chamber.

12. The method according claim 11 further comprising regulating a fluid flow rate of said fluid on a side opposite to said first pump with respect to said chamber.

13. The method according to claim 11 further comprising:
   providing a third value representative of the fluid flow rate through the second pump to a control device, and determining if the (i) second value is accurate or (ii) the third value is accurate by correlating said third value with said first value.

14. The method according to claim 13 wherein the first pump continues pumping while said second pump is activated and in that said second pump is activated at a flow rate greater to the predetermined first fluid flow rate.

15. The method according to claim 13 further comprising repeating cyclically the steps of continuously pumping the fluid by said first pump, pumping the fluid by said second pump, or letting the fluid pass through said second pump, and stopping said second pump, or stopping the fluid flow through said second pump.

16. The method according to claim 11 further comprising:
providing a third value representative of the fluid flow rate through the second pump to a control device, and
determining if (i) the second value is accurate or (ii) the third value is accurate by correlating said third value with said second value.

17. The method according to claim 16 further comprising regulating said first pump if the determination is that (i) said second value is inaccurate or (ii) the third value is inaccurate.

18. The method according to claim 16 further comprising regulating said second pump if the determination is that (i) said second value is inaccurate or (ii) the third value is inaccurate.

19. The method according to claim 11 further comprising:
continuously pumping the fluid by said first pump away from said chamber during a predetermined treatment period at a predetermined first fluid flow rate,
pumping the fluid by said second pump at a predetermined second fluid flow rate when a predetermined minimum threshold of said first value is reached, and
stopping said second pump when a predetermined maximum threshold of said first value is reached.

20. The method according to claim 11 further comprising:
continuously pumping the fluid by said first pump into said chamber during a predetermined treatment period at a predetermined first fluid flow rate;
pumping the fluid by said second pump at a predetermined second fluid flow rate superior to the predetermined first fluid flow rate, when a predetermined maximum threshold of said first value is reached, and
stopping said second pump when a predetermined minimum threshold of said first value is reached.

21. An apparatus for controlling a fluid flow rate in a fluid transport line which is a waste line of a medical device, comprising:
a fluid transport line;
a first pump disposed in said fluid transport line for pumping the fluid;
a chamber disposed in said fluid transport line for collecting said fluid;
a sensor for providing a first value correlated to the amount of fluid in said chamber;
a control device configured for (i) receiving a second value representative of the fluid flow rate through the first pump (ii) converting the first value into a fluid flow rate value, and (iii) determining if the second value is accurate by comparing the fluid flow rate value to the second value; and
a fluid flow regulator disposed in said fluid transport line for regulating the flow rate of said fluid on a side opposite said chamber from said first pump, said fluid flow regulator being also operatively connected to said control device, wherein the fluid flow regulator includes a second pump disposed in said fluid transport line for pumping a fluid on the opposite side of said first chamber.

22. The apparatus according to claim 21, wherein the sensor is a weight sensor configured for controlling the weight of the fluid in said chamber or a level sensor configured for controlling the level of the fluid in said chamber.

23. The apparatus according to claim 21, wherein said first pump is continuously activated during a predetermined treatment period, and wherein a predetermined minimum threshold and a maximum threshold are provided for said first value, said fluid flow regulator or second pump being activated by said control device when said maximum threshold is reached and being inactivated when said minimum threshold is reached, said fluid flow regulator or second pump providing, when activated, a fluid flow rate superior to the fluid flow rate of said first pump.

24. A method for controlling a fluid flow rate in a fluid transport line which is a waste line of a medical device, comprising the steps of:
pumping a fluid through the fluid transport line by a first pump;
collecting said fluid passing in said transport line in a chamber;
sensing the amount of fluid in said chamber and generating a first value representative of the amount of fluid in said chamber;
sending the first value to a control device;
detecting and sending a second value representative of a fluid flow rate through the first pump to the control device;
converting the first value into a fluid flow rate value;
determining if the second value is accurate by comparing the fluid flow rate value to the second value; and
regulating a fluid flow rate of said fluid on a side opposite said first chamber from said first pump, the step of regulating including pumping the fluid with a second pump disposed in said fluid transport line on the side opposite said first chamber.

25. The method according to claim 24, further comprising:
continuously pumping the fluid by said first pump into said first chamber during a predetermined treatment period at a predetermined first fluid flow rate;
pumping the fluid by said second pump at a predetermined second fluid flow rate greater than the predetermined first fluid flow rate, when a predetermined maximum threshold of said first value is reached, and
stopping said second pump when a predetermined minimum threshold of said first value is reached.

26. An apparatus for controlling a fluid flow rate in a fluid transport line which is an infusion line of a medical device, comprising:
a fluid transport line;
a first pump disposed in said fluid transport line for pumping the fluid;
a chamber disposed in said fluid transport line for collecting said fluid;
a sensor for providing a first value correlated to the amount of fluid in said chamber;
a fluid flow regulator disposed in said fluid transport line for regulating the flow rate of said fluid on a side opposite said chamber from said first pump, wherein the fluid flow regulator includes a second pump disposed in said fluid transport line for pumping a fluid on the side opposite said first chamber;
a control device configured for (i) receiving a second value representative of the fluid flow rate through the first pump (ii) converting the first value into a fluid flow rate, and (iii) determining if the second value is accurate by comparing the fluid flow rate value to the second value; and a fluid flow regulator disposed in said fluid transport line for regulating the flow rate of said fluid on a side opposite said chamber from said first pump, said fluid flow regulator being also operatively connected to said control device, wherein the fluid flow regulator includes a second pump disposed in said fluid transport line for pumping a fluid on the side opposite said first chamber.

27. A method for controlling a fluid flow rate in a fluid transport line which is an infusion line of a medical device, comprising the steps of:

pumping a fluid through a fluid transport line by a first pump;

collecting said fluid passing in said transport line in a chamber;

sensing the amount of fluid in said chamber and generating a first value representative of the amount of fluid in said chamber;

sending the first value to a control device;

detecting and sending a second value representative of a fluid flow rate through the first pump to the control device;

converting the first value into a fluid flow rate value;

determining if the second value is accurate by comparing the fluid flow rate value to the second value; and regulating a fluid flow rate of said fluid on a side opposite said first chamber from said first pump, the step of regulating including pumping the fluid with a second pump disposed in said fluid transport line on the side opposite of said first chamber.

* * * * *